United States Patent [19]

Krajewski et al.

[11] 4,186,233
[45] Jan. 29, 1980

[54] DISPOSABLE COMPOSITE INSENSITIVE TO SURFACE MOISTURE BUT DISINTEGRATABLE IN AQUEOUS LIQUID

[75] Inventors: Richard M. Krajewski, St. Louis; Robert E. Erickson, Midland, both of Mich.

[73] Assignee: The Dow Chemical Company, Midland, Mich.

[21] Appl. No.: 890,159

[22] Filed: Mar. 27, 1978

[51] Int. Cl.² .................... B32B 7/02; A61F 13/16
[52] U.S. Cl. .................... 428/213; 428/518; 428/520; 428/523; 128/284; 128/156
[58] Field of Search ............... 428/413, 518, 520, 523; 128/284, 156; 260/88.1, 112, 73 R, 78 R

[56] References Cited

U.S. PATENT DOCUMENTS

| 3,669,103 | 6/1972 | Harper | 128/284 |
| 3,804,092 | 4/1974 | Tunc | 128/284 |
| 3,934,587 | 1/1976 | Gordon | 128/284 |
| 3,952,347 | 4/1976 | Comerford | 128/284 |
| 3,967,623 | 7/1976 | Butterworth et al. | 128/284 |
| 3,983,095 | 9/1976 | Bashaw et al. | 128/284 |
| 4,074,039 | 2/1978 | Lim et al. | 128/156 |

Primary Examiner—P. C. Ives

[57] ABSTRACT

A disposable composite comprising an absorbent, swellable film such as a lightly cross-linked polyacrylate, having on its two major surfaces a hydrophobic coating such as polyvinylidene chloride, is useful as a liner or packaging for disposable articles such as sanitary napkins. The hydrophobic coating protects the coated surfaces of the absorbent, swellable film from moisture, thereby maintaining the composite's integrity during use. Upon the composite's immersion in an aqueous fluid, the exposure of any uncoated film to water causes the composite to disintegrate, providing for easy flushability.

10 Claims, 3 Drawing Figures

DISPOSABLE COMPOSITE INSENSITIVE TO SURFACE MOISTURE BUT DISINTEGRATABLE IN AQUEOUS LIQUID

BACKGROUND OF THE INVENTION

This invention relates to disposable composites, in particular, to those composites which are insensitive to surface moisture, but which are easily disintegrated upon their immersion in an aqueous liquid.

Absorbent articles, such as disposable diapers and sanitary napkins, generally are constructed such that some portion of the article, usually the backing or liner, is a liquid repellent material. This repellent material is desired to minimize or prevent the exudation of the absorbed liquid from the article and to obtain lateral spreading of the absorbed liquid so that the absorbing capacity of the product may be more fully utilized. Liquid repellent materials commonly used heretofore include sheets and films of plastic materials, such as polyethylene films and the like. See, for example, U.S. Pat. Nos. 3,528,421 and 3,804,092.

Due to the nature of their use, it is hygienically undesirable to store the used articles with other refuse for commercial disposal. While disposal of such articles by flushing would be more convenient, the liquid repellent material, which normally does not disintegrate in water, tends to plug toilets and sewer pipes. Accordingly, it is necessary, although undesirable, to separate the repellent material from the article prior to flushing.

Moreover, the packaging in which the disposable articles are delivered are generally made from water-resistant materials. Water resistivity is necessary to prevent the degradation of the packaging from environmental conditions and to protect the disposable articles therein. Although this packaging is safely stored with other refuse for commercial disposal, they often are more conveniently flushed in the toilet with the discarded disposable article, thereby causing plugged drains and toilets.

Heretofore, several methods have been employed to overcome these deficiencies. In one conventional application, various water-dispersible materials are treated with a hydrophobic material to impart the desirable water-resistance properties thereto. For example, U.S. Pat. No. 3,510,587 discloses a disposable diaper having a backing of porous tissue, which has no wet strength, coated with a hydrophobic material such as oil, wax or resin. Similarly, U.S. Pat. No. 3,559,650 discloses a flush-disposable sanitary napkin having a backing of a water-disintegrating material coated on the side exposed to the absorbed fluid with a thin, flexible continuous layer of water-resistant material such as a greasy or oily material. In both instances, the water-resistant coating prevents the absorbed fluid from contacting the water-disintegrating material, thereby maintaining its integrity. Unfortunately, upon disposal in a toilet, the water-resistant materials are not disintegrated, thereby tending to cause the plugging of drains and toilets.

U.S. Pat. No. 3,350,592 proposes a method wherein the outer layer of a sanitary napkin is prepared from fibers or algenic acid and insoluble salts thereof, which are normally insoluble in water. When the napkin is discarded after use, a chemical such as sodium carbonate, is added to the water which changes the fibers to a soluble form by ion exchange. Although this method provides easy flushability of the napkin, the necessity of adding a chemical to the toilet following each use creates an undesirable inconvenience to the user.

In view of the stated deficiencies of the prior art, it remains highly desirable to provide a water-resistant material which degrades or otherwise disintegrates rapidly upon immersion in water, thereby facilitating flushability, but which retains its structural integrity until disposal is desired.

SUMMARY OF THE INVENTION

The present invention is such a disposable composite comprising an absorbent, swellable film of a water-insoluble, water-swellable polymer being sufficiently covered on its two major surfaces by a hydrophobic coating of a water-insoluble, water-impervious polymer to provide the film with suitable resistance to surface and environmental moisture. Accordingly, the hydrophobic coating prevents the absorbent, swellable film from absorbing water at environmental conditions or when the composite is exposed to an aqueous liquid on the coated surfaces. Thus, the composite can retain the desired integrity and structural strength under such conditions.

Surprisingly, however, upon immersion of the composite in an aqeuous liquid under conditions such that the film is exposed to excessive amounts of water, the composite disintegrates. In such disintegration the swellable film absorbs substantial amounts of water through exposed portions of the film, e.g., the ends of the composite which are often not coated with the hydrophobic coating. Upon absorption of substantial amounts of water, the film is converted to a weak, expanded gel-like material thereby breaking the hydrophobic coating into several pieces which separate from the film. This ability of the composite to disintegrate upon exposure to excessive amounts of water provides for easy flushability of the composite, i.e., reduces its tendency to plug drains, toilets, etc.

The disposable composites of this invention are particularly useful as packaging material wherein the package is conveniently disposed of in a toilet; for example, as a packaging material for a sanitary napkin or other catamenial devices. Moreover, the disposable composites are useful as backings or liners for many disposable articles, such as colostomy bags and disposable diapers.

BRIEF DESCRIPTION OF THE DRAWINGS

Understanding of the invention will be facilitated by referring to the accompanying drawings, in which.

DETAILED DESCRIPTION OF PREFERRED EMBODIMENTS

Figure 1:
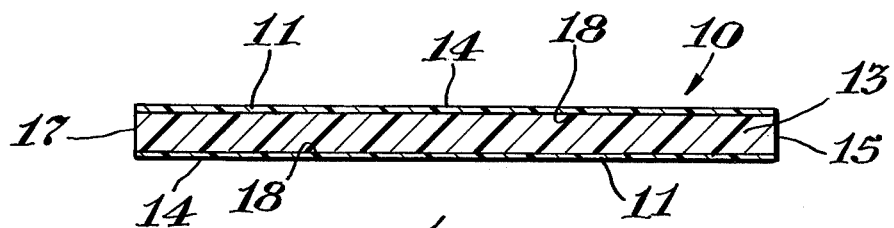
FIG. 1 is a cross-sectional schematic representation of a disposable composite of this invention prior to the exposure of the absorbent, swellable film to an aqueous liquid.

Referring now more particularly to the drawings, FIG. 1, which represents one embodiment of the invention, depicts a disposable composite 10 comprising an absorbent, swellable film 13 thinly coated on its two major surfaces 18 by a continuous hydrophobic coating 11. The hydrophobic coating 11 prevents water from permeating through its surface 14 onto the surface 18 of the absorbent, swellable film 13. Ends 15 and 17 of the composite are uncoated in this embodiment and provide sufficient exposure of the film 13 to enable disintegration of the composite upon its immersion in an aqueous liquid.

Figure 2:
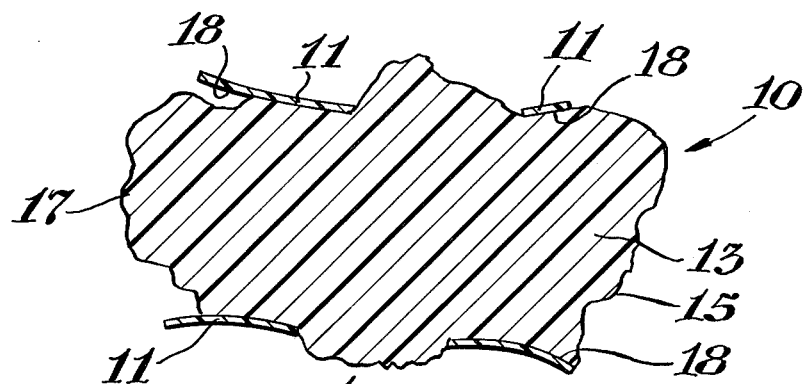
FIG. 2 is a cross-sectional schematic representation of a disposable composite of this invention after exposure of the film to an aqueous liquid.

FIG. 2 depicts a disposable composite 10 following the immersion of the disposable composite in an aqueous liquid. Water is absorbed by the absorbent, swellable film 13 through the uncoated ends 15 and 17 of the composite 10. The absorbence of the water by the absorbent, swellable film 13 causes the film 13 to expand to many times its original size. Upon the absorption of sufficient quantities of water, the subsequent expansion causes the thin hydrophobic coating 11 to disintegrate into smaller, more easily flushable pieces and to separate from the surface 18 of the absorbent film 13. The absorbent, swellable film 13 upon the absorption of sufficient quantities of water is also disintegrated, i.e., becomes a weak gel which breaks into relatively small pieces during flushing.

Figure 3:
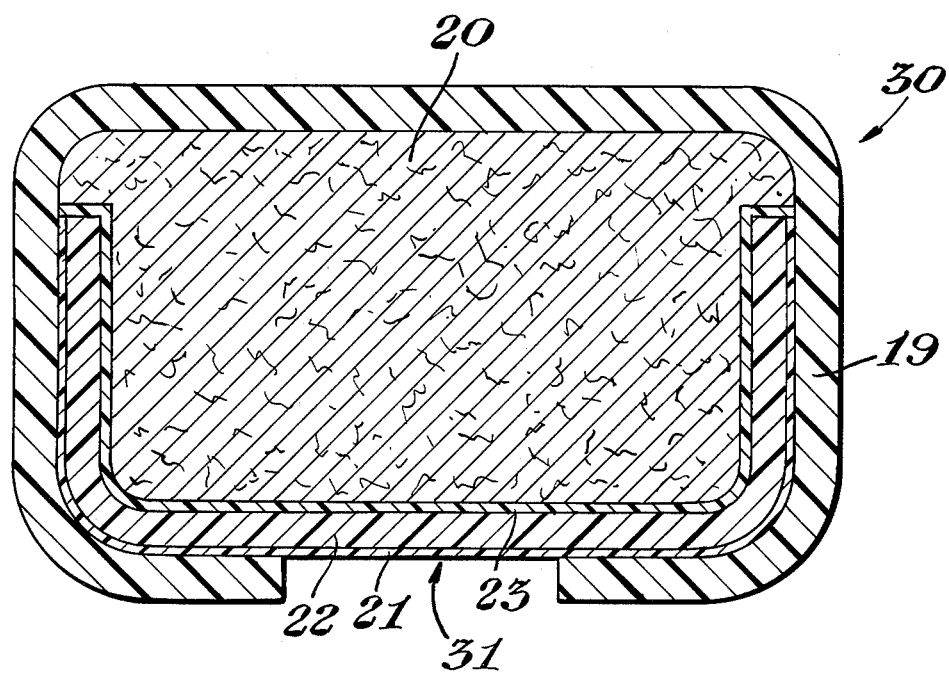
FIG. 3 is an enlarged cross-sectional schematic representation of one embodiment of the present invention, wherein the disposable composite of this invention is a backing for a sanitary napkin.

FIG. 3 depicts an embodiment of the present invention wherein a sanitary napkin 30 comprises a permeable layer 19 which lies adjacent to the skin, an absorbent core 20 and a backing 31 of the disposable composite of this invention. The backing 31 comprises a hydrophobic coating 21 which is exposed to environmental conditions, a hydrophobic coating 23 which is proximate to absorbent core 20 and an absorbent, swellable film 22 coated by hydrophobic coatings 21 and 23. In the practice of this invention, backing 31 becomes easily flushable upon the exposure of the absorbent, swellable film 22 to an aqueous liquid. Exposure of film 22 is easily accomplished by tearing of coating 21, providing discontinuities, e.g., ruptures, in coating 21 or other similar means. The disposable composite is easily incorporated in other disposable articles, e.g., colostomy bags, diapers and the like in much the same manner.

Although not shown by the drawings, the hydrophobic coating is also conveniently applied to three, four or more surfaces of the absorbent, swellable film depending on the particular requirements for preventing exposure of the film to surface or environmental moisture prior to immersion. As used herein, the term "immersion" is intended to mean immersion of the composite in excess amounts of an aqueous liquid, i.e., amounts in excess of those which the swellable film can absorb. Upon immersion, exposure of any portion of the swellable film to the aqueous liquid will cause disintegration of the composite. For example, when at least one surface of the absorbent, swellable film is uncoated, i.e., exposed, the film will absorb sufficient amounts of water during immersion to disintegrate the composite. Alternatively, when the absorbent, swellable film has no exposed portions, disintegration of the composite is readily accomplished by tearing the composite or other similar means which exposes the swellable film to the aqueous liquid during immersion. Preferably, to facilitate disintegration, the exposed areas of the film prior to immersion comprise at least about one percent, more preferably at least about two percent of the film's total surface area.

For the purpose of this invention, the absorbent, swellable film is a film of a water-insoluble, water-swellable polymer. Water-insoluble, water-swellable polymers are polymers, often referred to as hydrogels, having sufficient hydrophilic properties to absorb and hold water therein, but which are such that essentially none of the individual polymer molecules are disassociated from the bulk of the polymer when immersed in water, i.e., essentially none of the polymer forms a true solution in water. Upon the absorption of large amounts of water, i.e., more than 25 times the weight of the original, unswelled polymer, the water-insoluble, water-swellable polymers advantageously swell and exhibit a relatively soft gel-like consistency which is broken apart by the turbulence provided by a flushing toilet or the constricted flow of water through a pipe. Preferably, the water-insoluble, water-swellable polymers are capable of absorbing at least 50 times, more preferably at least 100 times their original, unswelled weight in water, with an approximate corresponding increase in volume.

Preferably, such water-insoluble, water-swellable polymers are lightly cross-linked polymers. Generally, the lightly cross-linked polymers suitably employed in the present invention are prepared by copolymerizing one or more water-soluble monomer, e.g., monomers which can form at least a 5 weight percent solution in water with a small amount of a polyfunctional cross-linking agent, and cross-linking said copolymer to a degree sufficient that the resulting lightly cross-linked polymer is water-insoluble but water-swellable. Typically, suitably employed polymers are copolymers of one or more vinyl monomers, wherein at least 50 mole percent of such monomers are water-soluble, with about 0.01 to about 10 mole percent of a cross-linking agent. Alternatively, a comparable degree of radiation-cure can be effectively employed. In yet another procedure, certain water-insoluble polymers, such as olefin-maleic anhydride copolymers, may be lightly cross-linked with an alkylene diamine or aliphatic diol and thereafter converted to an ammonium or alkali metal salt form to obtain the desired water-insoluble, water-swellable polymer.

Representative examples of lightly cross-linked polymers suitably employed in this invention include lightly cross-linked polymers of vinylpyrrolidone, vinylbenzene sulfonates, sulfoethyl acrylates or methacrylates, hydroxyalkyl acrylates, acrylic or methacrylic acids, acrylamide, methacrylamide, and the like and combinations thereof. Also suitably employed are the N-aminomethyl form (Mannich form) of polyacrylamide and the like, and the quaternized derivative of the Mannich derivative of polyacrylamide and the like.

Preferred lightly cross-linked polymers are lightly cross-linked polyacrylates prepared in accordance with the teaching of U.S. Pat. No. 3,926,891; the polymeric sorbents disclosed by U.S. Pat. No. 3,669,103; and the sorbent substances of U.S. Pat. No. 3,810,468, all of which are hereby incorporated by reference.

U.S. Pat. No. 3,926,891 teaches a method of making soft, absorbent, lightly cross-linked polyacrylate materials. Briefly summarized, the polyacrylates are prepared by saponifying an aqueous solution comprising (1) between about 30 to about 70 weight percent of a polyacrylate comprising (a) from about 30 to about 92 weight percent of an alkyl acrylate having 1–10 carbon atoms in the alkyl group or an alkyl methacrylate having 4–10 carbon atoms in the alkyl group, or mixtures thereof, (b) about 3 to about 70 percent of an olefinically unsaturated carboxylic acid, and (c) about 0 to about 15 percent of an omega hydroxyalkyl acrylate having 1–4 carbon atoms in the hydroxyalkyl group; and (2) an alkali metal hydroxide, at a concentration sufficient to saponify some of the acrylate esters and to neutralize the carboxylic acid groups. Following saponification, from about 0.1 to about 10 weight percent based on dissolved polymer of a cross-linking agent which is reactive with carboxylate salt groups is added.

U.S. Pat. No. 3,669,103 describes various lightly cross-linked polymers including polyvinylpyrrolidones, sulfonated polystyrenes, sulfonated polyvinyl toluenes, polysulfoethyl acrylates, poly-2-hydroxyethyl acrylates, polyacrylates, hydrolyzed polyacrylamides and copolymers of acrylamides with acrylic acid. U.S. Pat. No. 3,810,468 describes other lightly cross-linked swellable, water-insoluble polymeric sorbents including polyvinyl morpholinone; amides and alkali metal or ammonium salts derived from copolymers of maleic anhydride with vinyl methylether, with vinyl pyrrolidone, with vinyl morpholinone, or with mono-olefinic hydrocarbons; polymers and copolymers of acrolein modified by the reaction with an alkali metal hydroxide or alkali metal bisulfite and copolymers of sulfur dioxide with allyl alcohol, allyl ether of glycerol or allyl ether of ethylene glycol or a polyethylene glycol.

Especially preferred are the lightly cross-linked polyacrylate materials prepared in accordance with the method disclosed in U.S. Pat. No. 3,926,891.

Advantageously, in the practice of this invention, the absorbent, swellable film is prepared as a continuous sheet by methods described in the patents hereinbefore incorporated. In general, the absorbent, swellable films are easily prepared by conventional casting techniques. For example, an aqueous solution of the absorbent material can be spread on a flat plate or roller of metal, plastic or similar impervious substance prior to cross-linking. The solution is heated to lightly cross-link the polymer and drive off excess water. The absorbent film is then removed from the plate or roller by a scraper or similar means for subsequent use. In many applications, powder, flakes or fibers of the absorbent material are advantageously employed. These are also easily prepared by methods described in the patents hereinbefore incorporated by reference.

For the purposes of this invention, the hydrophobic coating is a water-insoluble, water-impervious polymer, which does not swell significantly when exposed to water, e.g., will not absorb more than about 0.5 times its volume in water. Moreover, the hydrophobic coating will disintegrate from the volume expansion of the film upon the film's exposure to excess water. By "disintegration of the hydrophobic coating" is meant that the hydrophobic coating will break into several smaller size pieces, e.g., 2 mm by 2 mm, and separate from the absorbent, swellable film, thereby being easily flushable in a conventional toilet or similar disposal means. By "water-insoluble" is meant that the polymer is essentially insoluble in water; i.e., essentially none of the polymer will form a true solution in water. A water-impervious polymer is any polymer which, when employed as a coating in the practice of this invention, is capable of preventing the seepage of water from its outer surface through to the absorbent, swellable film during use such that premature disintegration of the composite will not occur. Advantageously, the water-impervious polymers exhibit a water transmission rate (Q) of less than about 3000 grams of water per square meter in a 24 hour period at 40° C. and atmospheric pressure, i.e., 760 mm Hg when the polymer is employed as a 1 mil sheet. Preferably, the hydrophobic coating material possesses sufficient strength, both tensile and shear, to prevent rupture or perforation of the coating prior to and during use.

Examples of materials suitably employed as hydrophobic coatings include polyvinyl acetate; water-insoluble ethyl cellulose; polyvinylidene chloride, polyacrylates including polymers and copolymers of acrylic acid, methacrylic acid, esters of these acids and acrylonitrile; and the like. Preferably employed in this invention are the water-insoluble ethyl celluloses having from about 45 to about 49.5 percent ethoxyl by weight and from about 10 to about 100 cps viscosity as measured on a Ubbelohde viscometer (1.1 mm inside diameter) at 25° C. as a 5 weight percent solution in an 80/20 toluene/ethanol mixture and polyvinyl chloride, with ethyl cellulose being especially preferred.

In preparing the composite, the hydrophobic coating is easily applied to the absorbent, swellable films by conventional application techniques such as spraying, brushing or other suitable techniques. Generally, a continuous coating is advantageously applied to the film. By the term "continuous coating" is meant a coating devoid of holes, scratches or other imperfections which may allow the swellable film to absorb amounts of water sufficient to cause premature disintegration of the composite. However, it is sometimes desirable to provide small holes in the hydrophobic coating to facilitate the disintegration of the disposable composite on its immersion in an aqueous liquid. This is especially desirable when a relatively thick or strong hydrophobic coating is employed or where the surfaces of the coating are not exposed to higher levels of moisture during use.

Spraying of the hydrophobic material as a dilute solution in a normally volatile organic solvent is the preferred method of application. A normally volatile organic solvent is a material which is a liquid at ambient temperatures and which exhibits a vapor pressure of at least 10 mm at 20° C. and 760 mm Hg pressure. Exemplary solvents for ethyl cellulose are the lower alkyl alcohols such as n-propanol, isopropanol, n-butanol and the like. For polyvinylidene chloride exemplary solvents are toluene and xylene. Following the application of the solution, the resulting composite is air dried or heated to temperatures sufficient to drive off excess solvent and dry the coating, with temperatures between about 20° and about 40° C. being advantageously employed.

Coating thicknesses most advantageously employed are dependent upon the strength and water transmission rates of the hydrophobic coating. Typically, as the water transmission rate of the hydrophobic coating increases, the thickness of the coating is advantageously increased to prevent the excess seepage of water through the coating to the absorbent, swellable film. Moreover, as the strength of the coating increases, the coating's thickness may beneficially be reduced provided that the water transmission rate of the coating is sufficient to protect the absorbent, swellable film from excessive surface and environmental moisture.

Moreover, the coating's thickness and strength, along with the swellability characteristics and initial volume of the film determine the disintegration rate of the composite. For example, as the capability of the swellable film to absorb water increases, thereby increasing its volume expansion upon immersion; stronger, thicker coatings are more easily disintegrated.

Typically, a continuous coating on the film's two major surfaces having a thickness between about 0.05 and about 0.2 times the thickness of the swellable film is advantageously employed. Generally, a continuous coating of a thickness between about 0.07 and about 0.15 times the thickness of the film is preferred. For example, a swellable film having a thickness of 2 mil and a capacity for absorbing 50 times its original, unswelled weight in water easily disintegrates a hydrophobic coating of a water-insoluble ethyl cellulose having a thickness of 0.3 mil.

In practice, the thickness of the coating and the absorbent, swellable film are also dependent on the particular application of the disposable composite. For example, using the composite as packaging for sanitary napkins and other catamenial devices, a continuous coating of polyvinylidene chloride with a thickness of from about 0.03 to about 1.0 mil is advantageously employed to provide sufficient water-resistance. In this application, an absorbent film of a polyacrylate prepared in accordance with U.S. Pat. No. 3,926,891, hereinbefore incorporated by reference, having a thickness of from about 0.5 to about 5.0 mil provides sufficient strength and volume expansion for the disintegration of the composite upon immersion. Using the same hydrophobic coating and absorbent film as a backing in disposable diapers, the backing being that layer furthest away from the baby's skin, an absorbent, swellable film of from about 1 to about 10 mil, is advantageously coated on the side nearer the baby's skin; with a hydrophobic coating having a thickness from about 0.1 to about 2 mil. On the other side, i.e., that surface exposed only to environmental conditions a hydrophobic coating having a thickness from about 0.03 to about 1 mil, is advantageously employed. Beneficially, in this application, the thickness is from about 1.2 to about 13 mil thick. For use in other applications, the thicknesses of the coating and film are easily determined by experimentation, as are the materials most advantageously employed to provide the benefits of this invention.

The following example is set forth to illustrate the invention and should not be construed to limit its scope. In the example, all parts and percentages are by weight unless otherwise indicated.

EXAMPLE

Three mixtures are prepared having the following composition:

| MIXTURE A | MIXTURE B | MIXTURE C |
| --- | --- | --- |
| 600 parts deionized water | 437.5 parts ethyl acrylate | 175 parts deionized water |
| 0.75 parts dioctyl-sodium sulfosuccinate | 77.2 parts methacrylic acid | 2.0 parts sodium bisulfite |
| 1.75 parts sodium persulfate | | |

To a 2 liter flask equipped with a thermocouple, thermometer, stirrer, heating device and addition funnel, is added Mixture A. The flask is then brought to a temperature of 40° C. while under a vigorous nitrogen purge. Eighteen parts of Mixture B are added to the flask followed by the addition of all of Mixture C. The remainder of Mixture B is added over the next 2.5 hours, while the temperature is held at 30°–40° C. The latex is then digested at 60° C. for 1.5 hours, the flask cooled to about 30° C. and the latex bottled. The latex contains about 40.6 percent non-volatiles.

An 1125-part portion of the above latex is added in a small stream over a period of 25 minutes to a slowly stirred solution of 187.2 parts of an aqueous solution of 50 percent NaOH in 547.9 parts deionized water. After the polymer has all dissolved, the viscous solution is heated at 50° C. for 22 hours to complete the saponification. The resulting solution (25.4 percent solids) has a Brookfield viscosity of about 16,200 cps at 25° C. (RVT Type, No. 5 spindle, 10 rpm). The polymer is 50 percent ethylacrylate by moles with the remainder being sodium acrylate and methacrylate. The resulting product is denoted Preparation I in the following table.

An absorbent formulation of a lightly cross-linkable polymer is prepared by mixing the following ingredients:

|  | Parts dry weight | Parts wet weight |
| --- | --- | --- |
| Preparation I | 94 | 364.4 |
| Polyoxyethylene sorbitan monolaurate | 5 | 5.0 |
| Polycup 172* (diluted 2:1 with water) | 1 | 24.0 |
| Distilled water | — | 106.6 |

*A liquid adduct of epichlorohydrin and a polyamide-polyamine having about 12.5 percent solids, pH 4.6–4.9 and about 12.8 percent nitrogen sold by Hercules, Inc.

The mixing procedure consists of mixing Preparation I, distilled water, Polyoxyethylene sorbitan monolaurate and diluted Polycup 172 on an air powered blade mixer until homogeneous.

The resulting mixture of about 20 percent solids is cast on a silicone release coated glass plate and cured at about 125° C. for 5 minutes. The resulting 2 mil sheet is conditioned at 50 percent relative humidity and 23° C. for 24 hours and is employed as the absorbent, swellable film in this example. It is designated Polymer A in Table I.

Ethyl cellulose, being characterized by having about 48 to about 49.5 percent ethoxyl by weight and 100 cps viscosity as measured on a Ubbelohde viscometer (1.1 mm inside diameter) at 20° C. as a 5 weight percent solution in an 80/20 toluene/ethanol mixture is admixed with isopropanol to form a 10 percent solution. This mixture is heated to about 43° C. and sprayed on both major surfaces of the absorbent, swellable film such that a 0.2 to 0.3 mil continuous coating is formed. The ends of the film remain uncoated. The resulting composite is similar to that depicted in FIG. 1. For the purposes of this example, this composite is designated Sample No. 1.

Similar composites (Sample Nos. 3, 4 and 5) are made in the same manner using polymers as set forth in Table I which are water-soluble, e.g., form at least about a 5 weight percent solution in water. In addition, a composite denoted Sample 2 is made in a manner similar to Sample 1 except that polyvinylidene chloride is admixed with toluene to form a 10 percent solution and used as the hydrophobic coating material.

An uncoated absorbent film similar to the absorbent, swellable film used in Sample No. 1 is employed as a control and is designated Sample No. C in Table I.

A piece of each sample is tested for resistance to disintegration from water placed on the surface. A second piece of each sample is tested for its ability to disintegrate upon immersion in water. The results of this testing are shown in Table I.

TABLE I

| SAMPLE | C* | 1 | 2 | 3* | 4* | 5* |
| --- | --- | --- | --- | --- | --- | --- |
| ABSORBENT FILM | Polymer A | Polymer A | Polymer A | Polyoxyethylene | Methyl Cellulose | Polyvinyl Alcohol |
| HYDROPHOBIC COATING | None | Ethyl Cellulose | Polyvinylidene Chloride | Ethyl Cellulose | Ethyl Cellulose | Ethyl Cellulose |
| WATER SENSITIVITY | | | | | | |
| SURFACE RESISTANCE (1) | 30 seconds | 6 hours | 6 hours | No Separation | No Separation | No Separation |
| IMMERSION RESISTANCE (2) | 30 seconds | 30 min. | 30 min. | No Separation | No Separation | No Separation |

*Not an example of this invention.
(1) Surface Resistance is found by cutting a 7.6 × 7.6 cm piece of the sample to be tested, folding 1.2 cm of each edge upward and securing the corners with paper clips, thereby forming a rectangular dish. Into the dish, water is poured to a level of 0.6 cm. The dish with water is placed in an environmental chamber at 22° C. and 50 percent relative humidity. The dish is inspected at regular intervals for swelling of the absorbent film and separation or disintegration of the hydrophobic coating. Failure of the composite material is that time at which the film is completely swollen and the coating has been completely separated from the film. A sample designated by No Separation indicates no separation or disintegration of the coating occurred within 24 hours. Failure of the control is the time at which the film becomes fully swollen.
(2) The ability to disintegrate upon immersion of the samples in water (Immersion Resistance) is tested by immersing a 2.5 × 7.6 cm strip of the composite in water. The strip is inspected at regular intervals for separation and disintegration of the hydrophobic coating. Disintegration of the composite is taken as that time at which the film is completely separated from the absorbent film. A sample given a rating of No Separation indicates the sample exhibited the undesirable characteristic of no separation or disintegration of the coating after being immersed for 48 hours. Disintegration of the control is the time at which the film becomes fully swollen.

As evidenced by the data in the foregoing table, the disposable composites made in accordance with this invention readily disintegrate upon exposure of the absorbent film to water, but provide adequate protection of the absorbent film from moisture on the coated surfaces. In contrast, the films of the water-soluble, non-water-swellable polymers having a hydrophobic coating do not readily disintegrate in water.

What is claimed is:

1. A disposable composite comprising an absorbent, swellable film of a water-insoluble, water-swellable polymer being sufficiently covered on its two major surfaces by a hydrophobic coating of a water-insoluble, water-impervious polymer adapted to provide the film with resistance to surface and environmental moisture such that premature disintegration of the composite is prevented; the absorbent, swellable film being capable of absorbing an amount of water sufficient to convert the film into a weak, expanded gel-like material thereby breaking the hydrophobic coating into several pieces which separate from the film.

2. The disposable composite of claim 1 wherein the water-soluble, water-swellable polymer is a lightly cross-linked polymer.

3. The disposable composite of claim 2 wherein the absorbent, swellable film absorbs at least 50 times its original, unswelled weight in water upon the immersion of the disposable composite material in an aqueous liquid.

4. The disposable composite of claim 2 wherein the hydrophobic coating is from about 0.05 to about 0.2 times the thickness of the absorbent film.

5. The disposable composite of claim 4 wherein at least one percent of the film's total surface area is exposed prior to immersion.

6. The disposable composite of claim 5 wherein the hydrophobic coating is comprised of a material selected from the group consisting of polyvinyl acetate, water-insoluble ethyl cellulose, polyvinylidene chloride, and polyacrylate.

7. The disposable composite of claim 2 wherein the lightly cross-linked polymer is selected from the group consisting of lightly cross-linked polyacrylates; polyvinylpyrrolidones; sulfonated polystyrenes; sulfonated polyvinyl toluenes; polysulfoethyl acrylates; poly-2-hydroxyethyl acrylate; hydrolyzed polyacrylamides; copolymers of acrylamides with acrylic acid; polyvinyl morpholinone; amides and alkali metal or ammonium salts derived from copolymers of maleic anhydride with vinyl methylether, with vinylpyrrolidone, with vinyl morpholinone or with mono-olefinic hydrocarbons; polymers and copolymers of acrolein modified by the reaction with an alkali metal hydroxide or alkali metal bisulfite and copolymers of sulfur dioxide with allyl alcohol, allyl ether or glycerol or allyl ether of ethylene glycol or a polyethylene glycol.

8. The disposable composite of claim 2 wherein the lightly cross-linked polymer is derived from a cross-linkable polyacrylate solution prepared by (A) saponifying an aqueous solution comprising (1) between about 30 to 70 weight percent of a polyacrylate comprising (a) from about 20 to about 92 weight percent of an alkyl acrylate having 1-10 carbon atoms in the alkyl group or an alkyl methacrylate having 4-10 carbon atoms in the alkyl group, or mixtures thereof, (b) about 3 to about 70 percent of an olefinically unsaturated carboxylic acid, and (c) about 0 to about 15 percent of an omega hydroxyalkyl acrylate having 1-4 carbon atoms in the hydroxyalkyl group; and (2) an alkali metal hydroxide, at a concentration sufficient to saponify some of the acrylate esters and to neutralize the carboxylic acid groups, and (B) adding from about 0.1 to about 10 weight percent based on dissolved polymer of a cross-linking agent which is reactive with carboxylate salt groups.

9. The disposable composite of claim 3 wherein a one mil sheet of the water-insoluble, water-impervious polymer exhibits a water transmission rate of less than 3000 grams of water per square meter in a 24 hour period at 40° C. and 760 mm pressure.

10. The disposable composite of claim 9 wherein the hydrophobic coating is a continuous coating of the water-insoluble, water-impervious polymer.

* * * * *

UNITED STATES PATENT AND TRADEMARK OFFICE
CERTIFICATE OF CORRECTION

PATENT NO. : 4,186,233

DATED : January 29, 1980

INVENTOR(S) : Richard M. Krajewski; Robert E. Erickson

It is certified that error appears in the above–identified patent and that said Letters Patent are hereby corrected as shown below:

Column 1, line 63, delete "or" and insert --of--.

Column 2, line 25, delete "aqeuous" and insert --aqueous--.

Column 2, line 29, delete "e,g.," and insert --e.g.,--.

Column 3, line 64, delete "purpose" and insert --purposes--.

Column 7, line 32, after "conditions", insert a comma --,--.

Column 9, line 44, delete "water-soluble" and insert --water-insoluble--.

Column 10, line 41, after "30 to", insert --about--.

Signed and Sealed this

Third Day of June 1980

[SEAL]

Attest:

SIDNEY A. DIAMOND

Attesting Officer

Commissioner of Patents and Trademarks